United States Patent

Heywang et al.

Patent Number: 5,144,081
Date of Patent: Sep. 1, 1992

[54] DIALKOXYBENZYLIDENE-CAMPHOR DERIVATIVES

[75] Inventors: Ulrich Heywang, Darmstadt; Roland Martin, Weinheim; Ingeborg Stein, Erzhausen, all of Fed. Rep. of Germany

[73] Assignee: Merck Patent Gesellschaft Mit Beschrankter Haftung, Darmstadt, Fed. Rep. of Germany

[21] Appl. No.: 754,844

[22] Filed: Sep. 4, 1991

[30] Foreign Application Priority Data

Sep. 4, 1990 [DE] Fed. Rep. of Germany ....... 4027980

[51] Int. Cl.$^5$ .......................................... C07C 119/537
[52] U.S. Cl. ..................................... 568/326; 562/100
[58] Field of Search ....................... 562/100; 568/326; 514/692

[56] References Cited

U.S. PATENT DOCUMENTS 4,663,088 5/1987 Lang et al. ........................... 562/100

FOREIGN PATENT DOCUMENTS 0390682 10/1990 European Pat. Off. ............ 562/100

Primary Examiner—Marianne Cintins
Assistant Examiner—John Peabody
Attorney, Agent, or Firm—Millen, White & Zelano

[57] ABSTRACT

The invention relates to dialkoxybenzylidene-camphor derivatives of the formula I

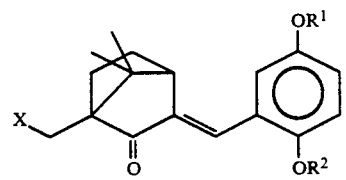

in which
$R^1$ and $R^2$, in each case independently of one another, are a straight-chain or branched alkyl radical having 1 to 10 c atoms, and
X is H or $SO_3H$, and to a process for their preparation and their use in cosmetic and pharmaceutical preparations.

9 Claims, No Drawings

DIALKOXYBENZYLIDENE-CAMPHOR DERIVATIVES

BACKGROUND OF THE INVENTION

The invention relates to the dialkoxybenzylidenecamphor derivatives of the formula I

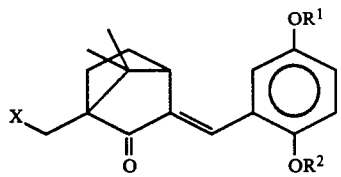

in which
$R^1$ and $R^2$, in each case independently of one another, are a straight-chain or branched alkyl radical having 1 to 10 C atoms, and
X is H or $SO_3H$
and to a process for their preparation and their use in cosmetic preparations, in particular for protection from solar radiation, and in pharmaceutical preparations for the prophylactic treatment of inflammations and allergies of the skin or certain types of cancer.

As is known, the skin has a sensitive reaction to solar rays, which can cause ordinary sunburn or erythema, but also more or less pronounced burning.

Solar rays, however, have other negative effects: they cause the skin to lose its elasticity and to form wrinkles and thus lead to premature aging. In some cases, dermatoses can also be observed. In the extreme case, certain types of skin cancer, such as melanoma, occur in some people.

It is also desirable to protect hair against photochemical damage in order to prevent changes in color shades, bleaching or damage of a mechanical type.

It is known that components contained in cosmetic preparations are not always sufficiently stable to light and decompose under the action of light rays.

As is known, the most hazardous part of the solar rays is formed of the ultraviolet rays having a wavelength of less than 400 nm. It is also known that owing to the presence of the ozone layer of the earth's atmosphere, which absorbs a part of the solar radiation, the lower limit of the ultraviolet rays which reach the earth's surface is at about 280 nm.

It thus appears desirable to make available compounds which can absorb UV rays in a wavelength range from 280 to 400 nm, i.e., also UV-B rays having a wavelength between 280 and 320 nm, which play a decisive role in the formation of sun erythema, and also UV-A rays having a wavelength between 320 and 400 nm, which can tan and also age the skin, promote the induction of an erythematous reaction or increase this reaction in certain people or can even induce phototoxic or photoallergic reactions.

The sunscreen filters customary nowadays in cosmetics are divided into UVA and UVB filters. While in the UVB range (280–320 nm), substances such as Eusolex ® 6300 (3-(4-methylbenzylidin)-camphor) or Eusolex ® 232 (4-phenyl-benzimidazole-5-sulfonic acid) make good filters, those used in the UVA range (320–400 nm) are affected by problems: Dibenzoylmethanes such as Parsol ® 1789 (butylmethoxydibenzoylmethane) or Eusolex ® 8020 (isopropyldibenzylmethane) are not indefinitely stable under UV irradiation, which on the one hand reduces the filter effectiveness with time and on the other hand can promote photosensitization of the skin in isolated cases. The benzophenones also used as UVA filters are only soluble to a limited extent in the oils used in cosmetics, and they have a relatively low absorption. On the other hand, only a few water-soluble UVA filters are known at present whose UV absorption, however, is low.

Similar benzylidenecamphor derivatives are disclosed in DE-OS 3,833,706. However, these have at least one tertiary alkyl group. These compounds can also be used as UV filters in sunscreen compositions, but, because of the phenolic hydroxyl group, are rather more suitable as antioxidants. Because of their tertiary alkyl group, these compounds are only soluble to a limited extent in conventional cosmetic vehicles, in particular in aqueous suspensions, so that in sunscreen compositions they always have to be employed together with other UV filters.

SUMMARY OF THE INVENTION

It has been found that 3-(2',5'-dialkoxybenzylidene)-camphor, in particular 3-(2',5'-dimethoxybenzylidene)-camphor, has outstanding UVA filter properties. Its solubility in the oils used in cosmetics is very good, so that use concentrations up to at least 10% of the preparation are possible even in complicated formulations. 3-(2',5'-dialkoxybenzylidene)camphor-10-sulfonic acids are a water-soluble form of the novel filter. The water solubility is so good here that use concentrations of 10% are likewise possible.

The absorption additionally has a minimum in the UVB range; however, this is not a disadvantage as a UVB filter can additionally be incorporated into the formulation without problems.

Furthermore, the compounds of the formula I can also be used for the prophylactic treatment of inflammations and allergies of the skin and for the prevention of certain types of cancer.

In addition to their good properties as filters, the compounds according to the invention are distinguished by good thermal and photochemical stability.

These compounds furthermore have the advantage of being non-toxic or non-irritant and completely harmless to the skin.

They are distributed uniformly in the conventional cosmetic vehicles and can form a continuous film, in particular in lipid vehicles; they can be applied to the skin in this way in order to form an effective protective film.

The invention relates to the compounds of the formula I given above.

In this formula, $R^1$ and $R^2$ are, for example, a methyl, ethyl, n-propyl, i-propyl, n-butyl, i-butyl, t-butyl or 1,1,3,3-tetramethylbutyl radical.

The preferred compounds of the general formula I include:
3-(2',5'-dimethoxybenzylidene)camphor
3-(2',5'-diethoxybenzylidene)camphor
3-(2',5'-dipropoxybenzylidene)camphor
3-(2',5'-dimethoxybenzylidene)camphor-10-sulfonic acid
3-(2',5'-diethoxybenzylidene)camphor-10-sulfonic acid
3-(2',5'-dipropoxybenzylidene)camphor-10-sulfonic acid.

The compounds of the formula I are obtained, for example, by condensing an aromatic aldehyde of the formula II

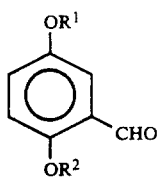

in which R¹ and R² have the meaning indicated in formula I, with natural or synthetic camphor or camphor-10-sulfonic acid in the presence of an inorganic base or a dialkylacyloxyborane.

As a rule, 0.9 to 2.0 moles, preferably 1.0 to 1.3 moles, of dialkoxybenzaldehyde of the formula II are reacted with 1.0 mole of camphor.

As a rule, 0.4 to 1.2 moles, preferably 0.5 to 1.0 moles, of dialkoxybenzaldehyde of the formula II are reacted with 1.0 mole of camphor-10-sulfonic acid.

The aldehydes of the formula II are prepared by known methods.

The compounds of the formula II preferably are prepared from the corresponding p-dialkoxyhydroquinones by reaction with 1,1-dichlorodimethylether in the presence of a Lewis acid, preferably $SnCl_4$ or $TiCl_4$, most preferred $TiCl_4$, according to Houben-Weyl, "Methods of Organic Chemistry," Vol. E3, page 23.

The condensation of the aldehyde II with camphor may preferably be carried out by one of the two following methods:

1st Method

The condensation is carried out in the presence of an alkali metal alkoxide, such as sodium methoxide or potassium t-butoxide, in a solvent, such a toluene, at the reflux temperature of the solvent. The condensation can also be carried out in the presence of an inorganic base, such as an alkali metal amide or hydride, in the presence of a solvent, such as dimethoxyethane, and at the reflux temperature of the solvent.

2nd Method

The condensation of the aldehyde II with camphor is carried out in the presence of a borane of the following formula III

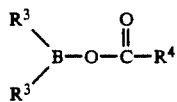

in which
R³ is an alkyl radical having 1 to 6 carbon atoms, and
R⁴ is an alkyl radical having 1 to 4 carbon atoms.

This compound is obtained by the method described in J. Am. Chem. Soc. 87, 1236 (1965). It is not necessary to isolate and to purify the compound in order to carry out the condensation of the aldehyde II with camphor.

The condensation is carried out with solvent at a temperature of 140°–160° C.

The invention also relates to the process for the preparation of the novel compounds of the formula I.

The process furthermore relates to a cosmetic preparation which contains an effective amount of at least one benzylidenecamphor derivative of the above formula I in a cosmetically tolerable vehicle.

Particularly preferred cosmetic preparations are those in which the vehicle has at least one lipid phase and X is H in the compound of formula I, or those in which the vehicle has at least one aqueous phase and X is $SO_3H$.

The cosmetic composition according to the invention can be used as a composition for protection of the human epidermis or the hair or as a sunscreen composition.

The invention furthermore relates to a method for protecting the skin and natural or sensitized hair from solar rays, in which an effective amount of at least one compound of the formula I is applied to the skin or the hair.

By "sensitized hair" is meant hair which has been subjected to a permanent wave treatment, a coloring process or a bleaching process.

The invention furthermore relates to a colored or uncolored light-stabilized cosmetic preparation which includes an effective amount of at least one benzylidenecamphor derivative of the above formula I.

If the cosmetic composition according to the invention is used as a composition for the protection of human epidermis against UV rays, it is present in various forms customarily used for this type. Thus, it can be present in particular in the form of oily or oily-alcoholic lotions or emulsions, such as cream or as milk, in the form of oily-alcoholic, oily-aqueous or aqueous-alcoholic gels or as solid sticks, or can be formulated as an aerosol.

It can contain cosmetic adjuvants which are customarily used in this type of composition, such as, for example, thickeners, softeners, humectants, surface-active agents, preservatives, antifoam agents, perfumes, waxes, lanolin, propellants, colorants and/or pigments which color the composition itself or the skin, and other ingredients usually used in cosmetics.

The compound of the formula I is generally present in an amount of 1 to 10%, relative to the total weight of the cosmetic composition for the protection of human epidermis.

The solubilizer used can be an oil, wax or other fatty material, a lower monoalcohol or a lower polyol or mixtures thereof. The particularly preferred monoalcohols or polyols include ethanol, i-propanol, propylene glycol, glycerol and sorbitol.

A preferred embodiment of the invention is an emulsion which is present as a protective cream or milk and includes fatty alcohols, fatty acid esters, in particular triglycerides of fatty acids, fatty acids, lanolin, natural or synthetic oils or waxes and emulsifiers in the presence of water in addition to the compound of the formula I.

Other preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycol, such as propylene glycol, and/or a polyol, such as glycerol, and oils, waxes and fatty acid esters, such as triglycerides of fatty acids.

The cosmetic composition according to the invention can also be present as an alcoholic gel which includes one or more lower alcohols or polyols, such as ethanol, propylene glycol or glycerol, and a thickener, such as silica. The oily-alcoholic gels additionally contain natural or synthetic oil or wax.

The solid sticks are composed of natural or synthetic waxes and oils, fatty alcohols, fatty acid esters, lanolin and other fatty materials.

The invention also relates to cosmetic sunscreen compositions which contain at least one compound of the formula I and can include other UVB and/or UVA filters.

About 2-20% by weight, preferably 3-15% by weight of the compound of formula I can be used to screen rays and achieve a beneficial effect, regardless of the carrier used.

In this case, the amount of the filter of the formula I is generally between 1.0 and 8.0% by weight, relative to the total weight of the sunscreen composition.

If a composition is formulated as an aerosol, the customary propellants, such as alkanes, fluoroalkanes and chlorofluoroalkanes are generally used.

If it is intended for the composition according to the invention to protect natural or sensitized hair from UV rays, it can be present as a shampoo, lotion, gel or emulsion for rinsing out, the respective formulation being applied before or after shampooing, before or after dyeing or bleaching, or before or after permanent waving; or the agent is present as a lotion or gel for hairdressing and treating, as a lotion or gel for brushing or setting a water-wave, as a hair lacquer, permanent-wave composition, or hair-dyeing or -bleaching composition. In addition to the compound according to the invention, this composition can contain various adjuvants used in this type of composition, such as surface-active agents, thickeners, polymers, softening compositions, preservatives, foam stabilizers, electrolytes, organic solvents, silicone derivatives, oils, waxes, anti-grease compositions, colorants and/or pigments which color the composition itself or the hair or other ingredients customarily used for hair case. The composition generally contains 1.0 to 5.0% by weight of the compound of the formula I.

The present invention also concerns cosmetic compositions which contain at least one compound of the formula I as compositions for protection from UV rays and as antioxidants; these compositions include hair products, such as hair lacquers, water-wave lotions for setting the hair, if appropriate for treatment or easier hairdressing, shampoos, dyeing shampoos, hair colorants, cosmetic products, such as nail varnish, creams and oils for skin treatment, make-up (foundation cream), lipsticks, skin care compositions, such as bath oils or creams and other cosmetic compositions which with respect to their components can raise problems with light stability and/or oxidation in the course of storage. Compositions of this type generally contain 1.0 to 5.0% by weight of a compound of the formula I.

The invention is furthermore concerned with a process for the protection of the cosmetic compositions from UV rays and oxidation, in which an effective amount of at least one compound of the formula I is added to these compositions.

The invention further relates to the use of the compounds of the formula I as sun filters with a large width of absorption in a wavelength range from 320 to 400 nm.

The invention further relates to the use of the compounds of the formula I as cosmetic products.

As already mentioned above, the applicant int eh course of his investigations has additionally found that the compounds of the formula I have a significant pharmacological activity in the field of preventive treatment of inflammations and skin allergies. The compound is also used against skin cancer which is caused by UV radiation, especially against melanomas.

The invention also relates to the compounds of the formula I for use as a medicament.

The compounds of formula I may be applied neat, i.e., without a carrier.

The invention furthermore relates to a pharmaceutical composition which contains an effective amount of at least one compound of the formula I in a non-toxic vehicle or excipient as the active compound.

The pharmaceutical composition according to the invention can be administered topically.

For topical administration, it is present as an ointment, cream, hair cream, solution, lotion, gel, spray, suspension, etc.

This composition can contain inert or pharmacodynamically active additives, in particular hydrating agents, antibiotics, steroidal or non-steroidal anti-inflammatory agents, carotinoids and agents against psoriasis.

This composition can also contain flavor-enhancing agents, preservatives, stabilizers, moisture regulators, pH regulators, modifiers of the osmotic pressure, emulsifiers, local anesthetics, buffers, etc.

It can additionally be formulated in a manner known per se in sustained-release form or in a form in which the active compound is rapidly released.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 40 27 980.4, are hereby incorporated by reference.

EXAMPLES

Example 1

DL-3-(2'-5'-Dimethoxybenzylidene)camphor

A suspension of 9.2 g (0.17 mol) of sodium methoxide in 200 ml of cyclohexane is initially introduced into an apparatus rendered inert with nitrogen and the mixture is treated with a solution of 18.2 g (0.12 mol) of DL-camphor in 100 ml of cyclohexane. The mixture is heated to 50° C. with stirring and 25 g (0.15 mol) of molten 2,5-dimethoxybenzaldehyde are then added. The reaction mixture is heated under reflux for 3 hours. After cooling, it is treated with 300 ml of water. The organic phase is separated off, washed with 1N hydrochloric acid and then with saturated sodium chloride solution, and dried over sodium sulfate. After removing cyclohexane in vacuo, 17.1 g of crude product are obtained. Excess DL-camphor is removed by steam distillation. After chromatography on silica gel 60 using toluene/ethyl acetate in the ratio 3:1 as the eluent, an oil is obtained which after some time solidifies to give 9.2 g of crystalline 3-(2',5'-dimethoxybenzylidene)camphor of melting point 70°-72° C.

The substance has IR, NMR and mass spectra which correspond to the expected structure.

UV (isopropanol) $\lambda max_1 = 287$ nm, $\epsilon = 12,000$. $\lambda max_2 = 352$ nm, $\epsilon = 6,500$.

The following are prepared analogously:
D-(+)-3-(2',5'-dimethoxybenzylidene)camphor. Melting point 95°–98° C., $[\alpha]^{20}{}_d = +388.1°$ (c=1, ethanol)
DL-3-(2',5'-diethoxybenzylidene)camphor
DL-3-(2',5'-di-n-propoxybenzylidene)camphor
DL-3-(2',5'-diisopropoxybenzylidene)camphor
DL-3-(2',5'-di-n-butoxybenzylidene)camphor
DL-3-(2',5'-di-tert-butoxybenzylidene)camphor
DL-3-(2',5'-di-n-hexyloxybenzylidene)camphor

Example 2

DL-3-(2',5'-dimethoxybenzylidene)camphor-10-sulfonic acid 46.5 g (0.2 mol) of DL-camphor-10-sulfonic acid (anhydrous) are initially introduced into an apparatus rendered inert with nitrogen and 400 ml of toluene and 20 ml of methanol are added. 27.0 g (0.5 mol) of sodium methoxide are introduced into this solution and the mixture is heated to reflux. After 30 minutes, the solution obtained form 16.6 g (0.1 mol) of 2,5-dimethoxybenzaldehyde in 400 ml of a 3:1 mixture of toluene and methanol is added dropwise to the solution boiling under reflux within one hour. The mixture is then heated under reflux for a further 30 hours. The mixture is treated with 150 ml of half-concentrated hydrochloric acid until the pH is less than 3. The aqueous phase is separated off and extracted twice with ethyl acetate (in each case 100 ml). The combined organic phases are dried over $Na_2SO_4$ and then concentrated in vacuo (bath temperature about 40° C.) until the onset of crystallization. The crystal suspension which remains is kept overnight at −20° C. and then filtered off with suction. 20 g of DL-3-(2',5'-dimethoxybenzylidene)camphor-10-sulfonic acid of melting point 121°–123° C. are thus obtained.

The substance has IR, NMR and mass spectra which correspond to the expected structure.

UV (methanol): $\lambda max_1 = 258$ nm, $\epsilon = 8,400$. $\lambda max_2 = 286$ nm, $\epsilon = 13,400$. $\lambda max_3 = 352$ nm, $\epsilon = 7,400$.

The following are prepared analogously:
DL-3-(2',5'-diethoxybenzylidene)camphor-10-sulfonic acid
DL-3-(2',5'-di-n-propoxybenzylidene)camphor-10-sulfonic acid
DL-3-(2',5'-di-n-butoxybenzylidene)camphor-10-sulfonic acid
DL-3-(2',5'-di-n-hexyloxybenzylidene)camphor-10-sulfonic acid
DL-3-(2',5'-di-tert-butyloxybenzylidene)camphor-10-sulfonic acid
DL-3-(2',5'-diisopropoxybenzylidene)camphor-10-sulfonic acid In the following use examples A to D and H, in each case the following UV filters can alternatively be employed:

1.
  10% compound from Example 1
2.
  5% compound from Example 1
  2% benzophenone-3
  3% octyldimethyl p-aminobenzoate (octyldimethylpaba)
3.
  6% compound from Example 1
  3% 3-(4-methylbenzylidene)camphor
4.
  4% compound from Example 1
  1% octyltriazone
5.
  8% compound from Example 1
  6% octyl methoxycinnamate
6.
  6% compound from Example 1
  4% octyl salicylate
  2% 4-isopropyldibenzoylmethane
7.
  8% compound from Example 1
  2% benzophenone-3

The names of the companies indicated in brackets give the standard source of the respective ingredients.

Example A: Sunscreen Composition (O/W)

The following ingredients are mixed, and for homogenization are optionally heated to 70°–85° C.; the perfume oil is added at 35°–45° C.

|  | % by weight |
|---|---|
| UV filter | q.s. |
| Arlacel 165 "glycerol monostearate and POE stearate" (ICI, Essen) | 9.5 |
| Atlas G-1790 "polyoxyethylene(20) lanolin derivative" (ICI, Essen) | 6.60 |
| Lanette O "cetylstearyl alcohol" (Henkel AG) | 3.00 |
| Mobile paraffin oil (E. Merck) | 3.00 |
| Isopropyl myristate | 1.50 |
| Abil AV 20 | 1.00 |
| Antioxidant containing butylhydroxytoluene "Oxynex 2004" (E. Merck) | 0.02 |
| Allantoin (E. Merck) | 0.30 |
| Sorbitol "liquid Karion F" (E. Merck) | 6.00 |
| Disodium salt of ethylenediaminetetraacetic acid "Titriplex" (E. Merck) | 0.05 |
| Pantothenyl alcohol | 0.30 |
| Preservative (E. Merck) | 0.5 |
| Demineralized water | to 100 |

Example B: Sunscreen Milk (O/W)

|  | % by weight |
|---|---|
| UV filter | q.s. |
| Mixture of cetyldimethicone copolyol, polyglyceryl-4-isostearate and hexyl laurate "Abil WE 09" (Th. Goldschmidt) | 5.00 |
| Mobile paraffin oil (E. Merck) | 16.00 |
| Sodium chloride (E. Merck) | 2.00 |
| Glycerol (E. Merck) | 3.00 |
| Preservative (E. Merck) | q.s. |
| Water, demineralized | to 100 |
| Delaila perfume oil (Dragoco) | 0.50 |

The ingredients are mixed and optionally heated to 70°–85° C. for homogenization; the perfume oil is added at 35°–45° C.

Example C: Sunscreen Cream (W/O)

|  |  | % by weight |
|---|---|---|
| A | UV filter | q.s. |
|  | POE glycerol sorbitan oleostearate "Arlacel 581" (ICI) | 7.0 |
|  | Mobile paraffin oil (E. Merck) | 6.0 |
|  | PPG-15 stearyl ether and cyclo- | 2.0 |

|  | % by weight |
|---|---|
| methicone 10 "Arlamol S 7" (ICI) | |
| 020 Kevit wax "Lunacera M" (LW Fuller) | 5.0 |
| Cyclomethicone "Dow Corning 344" (Dow Corning) | 4.00 |
| Triglyceride oil "Miglyol 812" (Huls Troisdorf AG) | 2.00 |
| B  Glycerol (cat. No. 4093) (E. Merck) | 2.00 |
| Magnesium sulfate heptahydrate (E. Merck) | 0.17 |
| Preservative (E. Merck) | q.s. |
| Water, demineralized | to 100.00 |

The ingredients are homogenized at 70°–85° C.; the preparation is optionally perfumed at 35°–45° C.

Example D: Sunscreen Cream (O/W)

|  |  | % by weight |
|---|---|---|
| A  UV filter | | q.s. |
| Mixture of cetearyl alcohol and ceteareth-20 "Emulgade 100 Ni" (Henkel) | (2) | 10.00 |
| Mobile paraffin oil (E. Merck) | (1) | 2.00 |
| Dimethylsiloxane "Dow Corning 200 (100 cs)" | (3) | 0.50 |
| Oxynex 2004 (E. Merck) | (1) | 0.10 |
| B  Glycerol (E. Merck) | (1) | 5.00 |
| Titriplex III (E. Merck) | (1) | 0.10 |
| Preservative (E. Merck) | (1) | q.s. |
| Water, demineralized | | to 100.00 |

The ingredients are homogenized at 70°–85° C. The preparation is optionally perfumed at 35°–45° C.

Example E: Sunscreen Cream (O/W)

To neutralize Eusolex® 232, tris(hydroxymethyl)aminomethane is dissolved in water and Eusolex® 232 is added with stirring. After solution is complete, the residual ingredients are added at 75°–85° C. and homogenized. Cool with stirring and optionally perfume at 40° C.

|  |  | % by weight |
|---|---|---|
| Compound from Example 1 | | 5.00 |
| Stearic acid (E. Merck) | | 20.00 |
| Triglyceride oil "Miglyol 812" (Huls Troisdorf AG) | | 20.00 |
| UV filter 2-phenylbenzimidazol-5-sulfonic acid "Eusolex 232" (E. Merck) | | 1.50 |
| Tris(hydroxymethyl)aminomethane (E. Merck) | | 0.66 |
| Sorbitol "liquid Karion F" (E. Merck) | | 5.00 |
| Allantoin (E. Merck) | (1) | 0.20 |
| Triethanolamine (E. Merck) | (1) | 6.00 |
| Preservative (E. Merck) | (1) | q.s. |
| Water, demineralized | | to 100.00 |

The compound from Example 1 can also be replaced by a mixture of 3% compound from Example 1 and 2% 3-(4-methylbenzylidene)camphor.

Example F: Hairdressing Gel (Oil-Containing) with UV Filter

The compound from Example 1 can also be replaced by a mixture of 2% compound from Example 1 and 1% benzophenone-3 or 1% 3-(4-methylbenzylidene)camphor.

|  |  | % by weight |
|---|---|---|
| Compound from Example 1 | | 3 |
| Polyoxyethylene-30-cetylstearyl alcohol "Emulgin B 3" (Henkel AG) | (2) | 13.00 |
| Polyol fatty acid ester "Cetiol HE" (Henkel AG) | (2) | 20.00 |
| Eutanol G "Octyldecanol" (Henkel AG) | (2) | 5.00 |
| Preservative (E. Merck) | | q.s. |
| Water, demineralized | | to 100.00 |

The ingredients are mixed and homogenized at 70°–85° C. The preparation is optionally perfumed at 35°–45° C.

Example G: Hair Treatment with UV Filter (Cream O/W)

|  | % by weight |
|---|---|
| UV filter | 3.00 |
| Cetylstearyl alcohol "Lanette O" (Henkel AG) | 2.50 |
| Polyoxyethylene-20-stearyl alcohol "Emulgin B 2" (Henkel AG) | 1.00 |
| Wax ester (jojoba oil substitute) "Cetiol J 600" (Henkel AG) | 1.00 |
| N-Cetyl-N,N,N-trimethylammonium bromide (E. Merck) | 1.00 |
| Preservative (E. Merck) | q.s. |
| Water, demineralized | to 100.00 |

Preparation is carried out analogously to Example A.

The compound from Example 1 can also be replaced by a mixture of the compound from Example 1 (2%) and benzophenone-3 (1%) or 3-(4-methylbenzylidene)-camphor (1%).

Example H: Sun Oil

|  |  | % by weight |
|---|---|---|
| UV filter | | q.s. |
| POE-40-sorbitol septaoleate "Arlatone T" (ICI) | | 2.00 |
| Triglyceride oil "Miglyol 812" (Huls Troisdorf AG) | (3) | 16.00 |
| Di-n-butyl adipate "Cetiol B" (Henkel AG) | (4) | 22.50 |
| Isopropyl myristate (Henkel AG) | (4) | 7.50 |
| Mobile paraffin oil (E. Merck) | | to 100.00 |
| Antioxidant containing butylhydroxytoluene "Oxynex 2004" (E. Merck) | | 0.2 |
| Preservative | | q.s. |
| Perfume oil 72979 (Haarmann & Reimer) | | q.s. |

Preparation is carried analogously to Example A.

Example I: Sunscreen Gel (Aqueous-Alcoholic)

|  | % by weight |
|---|---|
| Aqueous Phase: | |
| Compound from Example 2 | 10.00 |
| Tris(hydroxymethyl)aminomethane (E. Merck) | 2.80 |
| Allatoin (E. Merck) | 0.20 |
| Sorbitol "liquid Karion F" (E. Merck) | 5.00 |
| Preservative | q.s. |
| Water, demineralized | to 100.00 |
| Alcoholic Phase: | |
| Perfume oil (Haarmann & Reimer) | 0.30 |
| POE-35 hydrogenated castor oil "Arlatone 980" (IC) | 1.00 |
| Carboxyvinyl polymer "Carbopol 940" (Goodrich) | 1.50 |

|  | % by weight |
|---|---|
| Water, demineralized | 35.50 |
| Triethanolamine (E. Merck) | 3.00 |
| Water, demineralized | 10.00 |
| Ethanol (96%) (E. Merck) | to 100.00 |

To neutralize the UV filter from Example 2, the tris(-hydroxymethyl)aminomethane is dissolved in water and the UV filter from Example 2 is added with stirring. After solution is complete, the residual raw materials are added and the mixture is heated to 75° C. until it dissolves. It is then cooled with stirring.

Example J: Sunscreen Cream (O/W)

|   |   |   | % by weight |
|---|---|---|---|
| A | UV filter |  | q.s. |
|   | Stearic acid (E. Merck) |  | 20.00 |
|   | Triglyceride oil "Miglyol 812" |  | 20.00 |
| B | Compound from Example 2 (E. Merck) | (1) | 10.00 |
|   | Tris(hydroxymethyl)aminomethane (E. Merck) | (1) | 2.80 |
|   | Sorbitol "liquid Karion F" (E. Merck) | (1) | 5.00 |
|   | Allantoin (E. Merck) | (1) | 0.20 |
|   | Triethanolamine (E. Merck) | (1) | 6.00 |
|   | Preservative (E. Merck) | (1) | q.s. |
|   | Water, demineralized |  | to 100.00 |

The following can alternatively be employed as UV filters:
3% 3-(4-methylbenzylidene)camphor or
5% octyldimethylpaba or
2% benzophenone-3 or
4% octyl methoxycinnamate Preparation To neutralize the UV filter from Example 2, the tris(-hydroxymethyl)aminomethane is dissolved in the water of phase B and the UV filter from Example 4 is added with stirring. After solution is complete, the residual raw materials of phase B are added and the mixture is heated to 80° C. Phase A is heated to 75° C. Phase B is slowly stirred into phase A. Homogenize. Cool with stirring and optionally perfume at 40° C.

Example K: Sunscreen Cream (O/W)

|   |   |   | % by weight |
|---|---|---|---|
| A | UV filter |  | q.s. |
|   | Stearic acid (E. Merck) |  | 20.00 |
|   | Triglyceride oil "Miglyol 812" (Huls Troisdorf) |  | 20.00 |
| B | Compound from Example 2 (E. Merck) | (1) | 5.00 |
|   | Sodium hydroxide (10% solution) (E. Merck) | (1) | 0.40 |
|   | Sorbitol "liquid Karion F" (E. Merck) | (1) | 5.00 |
|   | Allantoin (E. Merck) | (1) | 0.20 |
|   | Triethanolamine (E. Merck) | (1) | 6.00 |
|   | Preservative | (1) | q.s. |
|   | Water, demineralized |  | to 100.00 |

The following can alternatively be employed as UV filters:
3% 3-(4-methylbenzylidene)camphor or
5% octyldimethylpaba or
2% benzophenone-3 or
4% octyl methoxycinnamate Preparation For neutralization, the UV filter from Example 2 is stirred into the sodium hydroxide solution and the water of phase B. After solution is complete, the residual raw materials of phase B are added and the mixture is heated to 80° C. Phase A is heated to 75° C. Phase B is slowly stirred into phase A. Homogenize. Cool with stirring and optionally perfume at 40° C.

Example L: Sunscreen Cream (O/W)

|   |   |   | % by weight |
|---|---|---|---|
| A | UV filter |  | q.s. |
|   | Stearic acid (E. Merck) | (1) | 20.00 |
|   | Triglyceride oil "Miglyol 812" (Huls Troisdorf AG) | (2) | 20.00 |
| B | UV filter from Example 2 (E. Merck) | (1) | 5.00 |
|   | Sorbitol "liquid Karion F" (E. Merck) | (1) | 5.00 |
|   | Allantoin (E. Merck) | (1) | 0.20 |
|   | Triethanolamine (E. Merck) | (1) | 6.17 |
|   | Preservative (E. Merck) | (1) | q.s. |
|   | Water, demineralized |  | to 100.00 |

The following can be employed as UV filters:
3% 3-(4-methylbenzylidene)camphor or
5% octyldimethylpaba or
2% benzophenone-3 or
4% octyl methoxycinnamate Preparation To neutralize the UV filter from Example 2, the triethanolamine is dissolved in the water of phase B and the UV filter from Example 4 is added with stirring. After solution is complete, the residual raw materials of phase B are added and the mixture is heated to 80° C. Phase A is heated to 75° C. Phase B is slowly stirred into phase A. Homogenize. Cool with stirring and optionally perfume at 40° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A dialkoxybenzylidenecamphor compound of formula I

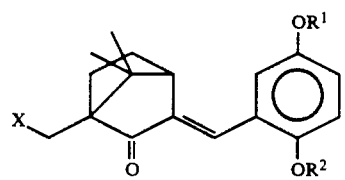

wherein
R$^1$ and R$^2$, in each case independently of one another, are a straight-chain or branched alkyl radical having 1 to 10 C atoms, and X is H or SO₃H.

2. A compound according to claim 1 which is 3-(2',5'-dimethoxybenzylidene)camphor, 3-(2',5'-diethoxybenzylidene)camphor or 3-(2',5'-dipropoxybenzylidene)-camphor.

3. A compound according to claim 1 which is 3-(2',5'-dimethoxybenzylidene)camphor-10-sulfonic acid, 3-(2',5'-diethoxybenzylidene)camphor-10-sulfonic acid or 3-(2',5'-dipropoxybenzylidene)camphor-10-sulfonic acid.

4. A cosmetic preparation comprising an effective amount of at least one compound of formula I

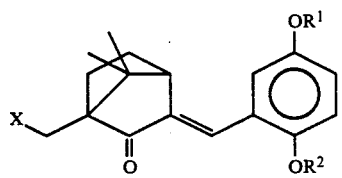

wherein
R¹ and R², in each case independently of one another, are a straight-chain or branched alkyl radical having 1 to 10 C atoms, and
X is H or SO₃H,
in a cosmetically tolerable vehicle.

5. A cosmetic preparation according to claim 4, wherein the vehicle comprises at least one lipid phase, and at least one compound of the formula I in which X is H.

6. A cosmetic preparation according to claim 4, wherein the vehicle comprises at least one aqueous phase, and at least one compound of the formula I in which X is SO₃H.

7. A cosmetic preparation according to claim 4, comprising 1 to 10% by weight of at least one compound of the formula I.

8. A cosmetic preparation according to claim 4, further comprising a UV-B filter selected from the group consisting of cinnamic acid derivatives, phenyl benzimidazole derivatives, p-aminobenzoic acid and benzylidene-camphor.

9. A pharmaceutical preparation for topical application comprising an effective amount of at least one compound of formula I

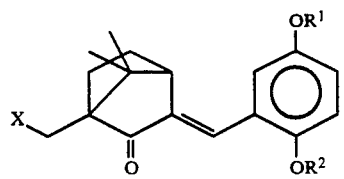

wherein
R¹ and R², in each case independently of one another, are a straight-chain or branched alkyl radical having 1 to 10 C atoms, and
X is H or SO₃H,
in a physiologically acceptable vehicle or excipient.

* * * * *